United States Patent [19]

Morphy et al.

[11] Patent Number: 5,714,491

[45] Date of Patent: Feb. 3, 1998

[54] PEPTIDYL DERIVATIVES AS METALLOPROTEINASE INHIBITORS

[75] Inventors: John Richard Morphy; Thomas Andrew Millican, both of Berkshire, United Kingdom

[73] Assignee: Celltech Therapeutics Limited, Berkshire, United Kingdom

[21] Appl. No.: 356,315

[22] PCT Filed: Apr. 27, 1994

[86] PCT No.: PCT/GB94/00895

§ 371 Date: Feb. 6, 1995

§ 102(e) Date: Feb. 6, 1995

[87] PCT Pub. No.: WO94/25434

PCT Pub. Date: Nov. 10, 1994

[30] Foreign Application Priority Data

Apr. 27, 1993 [GB] United Kingdom ............... 9308696

[51] Int. Cl.$^6$ .................. C07K 259/04; A61K 31/19; A61K 31/505
[52] U.S. Cl. .................. 514/256; 514/277; 514/365; 514/374; 514/385; 514/403; 514/428; 514/438; 514/461; 514/575; 544/242; 546/348; 548/205; 548/215; 548/335.1; 548/373.1; 548/517; 548/566; 549/59; 549/76; 549/496; 562/623
[58] Field of Search .................. 562/623, 9, 15, 562/426, 442, 465, 489; 564/152, 154; 560/24, 25, 9, 19, 55, 76; 546/348; 544/242; 548/517, 566, 335.1, 215, 205, 373.1; 549/59, 76, 496; 514/575, 256, 277, 365, 374, 385, 403, 428, 438, 461

[56] References Cited

FOREIGN PATENT DOCUMENTS

| | | |
|---|---|---|
| 0 489 577 | 6/1992 | European Pat. Off. . |
| 0489577 | 6/1992 | European Pat. Off. . |
| 91/02716 | 3/1991 | WIPO . |
| 92/09564 | 6/1992 | WIPO . |
| 9209564 | 6/1992 | WIPO . |

OTHER PUBLICATIONS

Wahl et al., Biochemistry and Inhibition of Collagenase and Stromelysin, Ann. Rep. Med. Chem., 1990, vol. 25, pp. 177–184.

Porter et al., "Organometallic Reagents In Organic Synthesis", Smithkline Beecham Research Symposium, Mar. 25–25, 1993.

Stack et al., "Comparison of Vertebrate Collagenase And Gelatinase Using a New Fluorogenic Substrate Peptide", The Journal of Biological Chemistry, vol. 264, No. 8, pp. 4277–4281, (1989).

Moses et al., "Inhibitors of Angiogenesis", Bio/Technology, vol. 9:630–634, (1991).

Folkman et al., "Angiogenic Factors", Science, vol. 235:442–447, (1987).

WessJohann et al., "A New Versatile Synthesis of Ring–Substituted 2–Cyclopropylglycines and Related Amino Acids", Chem. Ber., vol. 125:867–882, (1992).

Primary Examiner—Robert Gerstl
Attorney, Agent, or Firm—Foley & Lardner

[57] ABSTRACT

Peptidyl derivatives are disclosed that are orally active metalloproteinase inhibitors. The peptidyl derivatives have a selective gelatinase action, have a long duration of action, and are useful in the prophylaxis or treatment of diseases or disorders in which stromelysis, collagenase or gelatinase have a role, for example, in the treatment of cancer to control the development of tumor metastases.

9 Claims, No Drawings

PEPTIDYL DERIVATIVES AS METALLOPROTEINASE INHIBITORS

This application is a 371 of PCT/GB94/00895 filed Aug. 27, 1994.

FIELD OF THE INVENTION

This invention relates to a novel class of peptidyl derivatives, to processes for their preparation and to their use in medicine.

BACKGROUND TO THE INVENTION

In normal tissues, cellular connective tissue synthesis is offset by extracellular matrix degradation, the two opposing effects existing in dynamic equilibrium. Degradation of the matrix is brought about by the action of proteinases released from resident connective tissue cells and invading inflammatory cells, and is due, in part, to the activity of at least three groups of metalloproteinases. These are the collagenases, the gelatinases (or type-IV collagenases) and the stromelysins. Normally these catabolic enzymes are tightly regulated at the level of their synthesis and secretion and also at the level of their extracellular activity, the latter through the action of specific inhibitors, such as $\alpha_2$-macroglobulins and TIMP (tissue inhibitor of metalloproteinase), which form inactive complexes with metalloproteinases.

The accelerated, uncontrolled breakdown of connective tissues by metalloproteinase catalysed resorption of the extracellular matrix is a feature of many pathological conditions, such as rheumatoid arthritis, corneal, epidermal or gastric ulceration; tumour metastasis or invasion; periodontal disease and bone disease. It can be expected that the pathogenesis of such diseases is likely to be modified in a beneficial manner by the administration of metalloproteinase inhibitors and numerous compounds have been suggested for this purpose [for a general review see Wahl, R.C. et al Ann. Rep. Med. Chem. 25, 175–184, Academic Press Inc., San Diego (1990)].

Although numerous metalloproteinase inhibitors have been described, many have not been suitable for further development as medicines since they have lacked any useful activity when administered orally at pharmaceutically acceptable doses. What is therefore needed is a potent and selective orally active compound with a good duration of action.

SUMMARY OF THE INVENTION

We have now found a new class of peptidyl derivatives, members of which are metalloproteinase inhibitors and which, in particular, advantageously possess a potent and selective inhibitory action against gelatinase. In addition, compounds according to the invention have surprisingly good oral bioavailability, and after oral administration have an advantageously longer duration of action than related known compounds, such as those described in International Patent Specification No. WO92/09564.

Thus according to one aspect of the invention we provide a compound of formula (1)

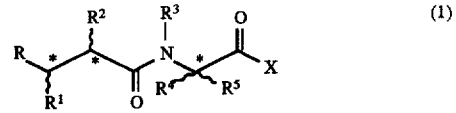

wherein

R represents a —CONHR$^6$ [where R$^6$ is a hydrogen atom or an acyl group], carboxyl (—CO$_2$H), esterified carboxyl, —SR$^6$ or —P(O)(X$_1$R$^7$)—X$^2$R$^8$ group, where X$^1$ and X$^2$, which may be the same or different, is each an oxygen or sulphur atom and R$^7$ and R$^8$, which may be the same or different each represents a hydrogen atom or an optionally substituted alkyl, aryl, or aralkyl group;

R$^1$ represents a hydrogen atom or an optionally substituted alkyl, alkenyl, aryl, aralkyl, heteroaralkyl or heteroarylthioalkyl group;

R$^2$ represents a group —Z$^2$(CH$_2$)$_m$Z$^1$—Ar wherein Ar is an aryl or heteroaryl group, Z$^1$ and Z$^2$, which may be the same or different, is each a bond or a heteroatom, and m is zero or an integer 1 to 6 with the proviso that when m is zero, Z$^2$ is a bond, and Z$^1$ is a heteroatom;

R$^3$ represents a hydrogen atom or an alkyl group;

R$^4$ represents a hydrogen atom or an alkyl group;

R$^5$ represents a group —C(R$_9$)(R$^{10}$)Het—R$^{11}$, wherein R$^9$ and R$^{10}$ which may be the same or different is each an optionally substituted alkyl or alkenyl group optionally interrupted by one or more —O— or —S— atoms or —N(R$^{12}$)— groups (where R$^{12}$ is a hydrogen atom or an optionally substituted alkyl group), or an optionally substituted cycloalkyl, cycloalkenyl, aryl or heteroaryl group, or R$^9$ and R$^{10}$ together with the carbon atom to which they are attached are linked together to form an optionally substituted cycloalkyl or cycloalkenyl group, Het is —O—, —S(O)$_p$—[where p is zero, or an integer 1 or 2] or —N(R$^{12}$)—, and R$^{11}$ is a hydrogen atom or an aliphatic, cycloaliphatic, heterocycloaliphatic, aromatic, or heteroaromatic group;

X is an amino (—NH$_2$), substituted amino, hydroxyl or substituted hydroxyl group, or is linked to the atom or group Het in R$^5$ to form a chain —X-Alk—R$^5$— where X is —N(R$_{12}$)—, Alk is an optionally substituted alkylene chain and R$^5$ is —Het—C(R$^9$)(R$^{10}$)—;

and the salts, solvates, hydrates and prodrugs thereof.

It will be appreciated that the compounds according to the invention can contain one or more asymmetrically substituted carbon atoms, for example those marked with an asterisk in formula (1). The presence of one or more of these asymmetric centres in a compound of formula (1) can give rise to stereoisomers, and in each case the invention is to be understood to extend to all such stereoisomers, including enantiomers and diastereoisomers, and mixtures, including racemic mixtures, thereof.

In the formulae herein, the ~line is used at a potential asymmetric centre to represent the possibility of R- and S-configurations, the ◀line and the ------- line to represent an unique configuration at an asymmetric centre.

In the compounds according to the invention, when the group R represents an esterified carboxyl group, it may be for example a group of formula —CO$_2$R$^{13}$ where R$^{13}$ is a straight or branched, optionally substituted C$_{1-8}$alkyl group such as a methyl, ethyl, n-propyl, i-propyl, n-butyl, i-butyl, s-butyl or t-butyl group; a C$_{6-12}$arylC$_{1-8}$alkyl group such as an optionally substituted benzyl, phenylethyl, phenylpropyl, $\alpha$-naphthylmethyl or $\beta$-naphthylmethyl group; a C$_{6-12}$aryl group such as an optionally substituted phenyl, α-naphthyl or β-naphthyl group; a $C_{6-12}$aryloxy $C_{1-8}$alkyl group such as an optionally substituted phenyloxymethyl, phenyloxyethyl, α- or β-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the groups $R_{13}$ include for example one or more halogen atoms such as fluorine, chlorine, bromine or iodine atoms, or $C_{1-4}$alkyl, e.g. methyl or ethyl, or $C_{1-4}$alkoxy, e.g. methoxy or ethoxy, groups.

In general, when the group R represents an esterified carboxyl group, it may be a metabolically labile ester of a carboxylic acid.

When the group $R^6$ in compounds of formula (1) represents an acyl group, it may be for example a group of formula $R^{14}C=X^3$ where $X^3$ is an oxygen or sulphur atom and $R^{14}$ represents a hydrogen atom or a group selected from amino (—$NH_2$), substituted amino (for example a group —$NR^{17}R^{18}$ as described below in relation to the group X), or an optionally substituted $C_{1-6}$alkyl, $C_{1-6}$alkoxy, $C_{1-6}$alkythio, $C_{2-6}$alkenyl, $C_{2-6}$alkynyl, $C_{6-12}$aryl, $C_{6-12}$aralkyl, $C_{3-6}$cycloalkyl, $C_{3-6}$heteroaryl or $C_{3-9}$heteroaralkyl group. Particular groups of these types include optionally substituted methyl, ethyl, n-propyl, i-propyl, methoxy, ethoxy, methylthio, ethylthio, ethenyl, 1-propenyl, ethynyl, 1-propynyl, phenyl, 1-naphthyl, 2-naphthyl, benzyl, phenethyl, 1-naphthylmethyl, 2-naphthylmethyl, cyclopropyl, cyclobutyl, cyclopentyl, cyclohexyl, furanyl, pyrrolyl, thienyl, furanylmethyl, pyrrolylmethyl or thienylmethyl groups. Optional substituents which may be present on such $R^{14}$ groups include one or more substituents selected from those described below in relation to the group $R^1$ or $R^2$ when such groups represent substituted alkyl, aryl or heteroaryl groups.

The group $R^7$ and/or $R^8$ in compounds of formula (1) may each be a hydrogen atom or an optionally substituted straight or branched $C_{1-6}$ alkyl, e.g. methyl, ethyl, n-propyl, i-propyl, n-butyl or i-butyl, $C_{6-12}$aryl, e.g. phenyl, or $C_{6-12}$aryl$C_{1-6}$alkyl, e.g. benzyl, phenylethyl or phenylpropyl group. Optional substituents present on alkyl groups of this type include one or more $C_{1-6}$alkoxy, e.g. methoxy or ethoxy, or $C_{1-6}$alkylthio, e.g. methylthio or ethylthio groups or an optionally substituted $C_{6-12}$aryloxy e.g. phenyloxy, $C_{6-12}$arylthio e.g. phenylthio, $C_{6-12}$aryl$C_{1-6}$alkoxy e.g. benzyloxy or $C_{6-12}$aryl$C_{1-6}$alkylthio e.g. benzylthio. Optional substituents present on the group $R^7$ or $R^8$ when it is an aryl or aralkyl group or an alkyl group substituted by an aryloxy or arylthio group include $R^{16}$ groups as defined below.

When the group $R^1$ in compounds of formula (1) represents an optionally substituted alkyl or alkenyl group, it may be, for example, a straight or branched $C_{1-6}$alkyl or $C_{2-6}$alkenyl group, such as a methyl, ethyl, n-propyl, i-propyl, n-butyl, i-butyl, s-butyl, t-butyl, n-pentyl, i-pentyl, n-hexyl, ethenyl, 1-propenyl, 1-butenyl or 2-butenyl group optionally substituted by one or more $C_{1-6}$alkoxy , e.g. methoxy, ethoxy, propoxy, $C_{1-6}$alkyl thio, e.g. methylthio, ethylthio, propylthio, $C_{6-12}$aryl$C_{1-6}$alkoxy, e.g. phenyl $C_{1-6}$alkoxy such as benzyloxy, aralkylthio, e.g. phenyl $C_{1-6}$alkylthio such as benzylthio, amino (—$NH_2$), substituted amino, [such as —$NHR^{15}$, where $R^{15}$ is a $C_{1-6}$ alkyl e.g. methyl or ethyl, $C_{6-12}$ aryl $C_{1-6}$alkyl, e.g. phenyl $C_{1-6}$alkyl, such as benzyl, $C_{6-12}$aryl, e.g. phenyl, $C_{3-8}$cycloalkyl, e.g. cyclohexyl, or $C_{3-8}$cycloalkyl$C_{1-6}$alkyl, e.g. cyclohexyl methyl group], carboxyl (—$CO_2H$ ) or —$CO_2R^{13}$ [where $R^{13}$ is as defined above] groups.

Aryl groups represented by $R^1$ in compounds of formula (1) include optionally substituted mono- or bicyclic $C_{6-12}$ aryl groups such as phenyl or 1- or 2-naphthyl groups.

Aralkyl groups represented by $R^1$ include optionally substituted mono- or bicyclic $C_{6-12}$aryl$C_{1-6}$alkyl groups such as phenyl$C_{1-6}$alkyl , or 1- or 2-naphthyl$C_{1-6}$alkyl , for example benzyl, phenylethyl, phenylpropyl, phenylbutyl, phenylpentyl, 1- or 2-naphthylmethyl, naphthylethyl, naphthylpropyl, naphthylbutyl or naphthylpentyl groups.

When the group $R^1$ in compounds of formula (1) is a heteroaralkyl group, it may be for example an optionally substituted mono- or bicyclic $C_{3-9}$heteroaryl$C_{1-6}$alkyl group, such as an optionally substituted pyrrolylmethyl, furanylmethyl, thienylmethyl, imidazolylmethyl, oxazolylmethyl, thiazolylmethyl, pyrazolylmethyl, pyridinylmethyl, or pyrimidinylmethyl group.

Heteroarylthioalkyl groups represented by $R_1$ include optionally substituted mono- or bicyclic $C_{3-9}$heteroarylthio$C_{1-6}$alkyl groups such as optionally substituted pyrrolylthiomethyl, furanylthiomethyl, oxazolylthiomethyl, thiazolylthiomethyl, pyrazolylthiomethyl, pyridinylthiomethyl, or pyrimidinylthiomethyl groups.

Optional substituents which may be present on aryl, aralkyl, heteroaralkyl or heteroarylthioalkyl groups represented by $R^1$ include those $R^{16}$substituents discussed below.

When the group Ar in compounds of formula (1) is an aryl group it may be an optionally substituted mono- or bicyclic $C_{6-12}$aryl group such as an optionally substituted phenyl, 1-naphthyl or 2-naphthyl group. When the group Ar is a heteroaryl group it may be an optionally substituted mono- or bicyclic $C_{3-9}$heteroaryl group containing one, two or three heteroatoms, selected from —O— or —S—, or —$N(R^{12})$— groups. Particular examples include optionally substituted pyrrolyl, furanyl, thienyl, imidazolyl, oxazolyl, thiazolyl, pyrazolyl, pyridinyl or pyrimidinyl groups. It will be appreciated that such groups may be connected to the remainder of the compound of formula (1) through any ring carbon atom, or where appropriate through a heteroatom or group —$N(R^{12})$—.

The aryl, aralkyl, heteroaryl, heteroaralkyl or heteroarylthioalkyl groups represented by $R^1$ and/or Ar in compounds of formula (1) may each optionally be substituted in the cyclic part of the group by one, two or more substituents [$R^{16}$] selected from halogen atoms, e.g. fluorine, chlorine, bromine or iodine atoms, or $C_{1-6}$alkyl, e.g. methyl or ethyl, $C_{1-6}$alkoxy e.g. methoxy or ethoxy, $C_{2-6}$alkylenedioxy, e.g. ethylenedioxy, halo$C_{1-6}$alkyl, e.g. trifluoromethyl, $C_{1-6}$alkyl amino, e.g. methylamino or ethylamino, $C_{1-6}$dialkylamino, e.g. dimethylamino or diethylamino, amino (—$NH_2$), nitro, cyano, hydroxyl (—OH), carboxyl (—$CO_2H$), —$CO_2R^{13}$, where $R^{13}$ is as defined above, $C_{1-6}$alkylcarbonyl, e.g. acetyl, sulphonyl (—$SO_3H$), $C_{1-6}$alkylsulphonyl, e.g. methylsulphonyl, aminosulphonyl (—$SO_2NH_2$), $C_{1-6}$ alkylaminosulphonyl, e.g. methylaminosulphonyl or ethylaminosulphonyl, $C_{1-6}$dialkylaminosulphonyl e.g. dimethylaminosulphonyl or diethylaminosulphonyl, carboxamido (—$CONH2$), $C_{1-6}$alkylaminocarbonyl, e.g. methylaminocarbonyl or ethylamino-carbonyl, $C_{1-6}$ dialkylaminocarbonyl, e.g. dimethylaminocarbonyl or diethylaminocarbonyl, sulphonylamino (—$NHSO_2H$), $C_{1-6}$alkylsulphonyl-amino, e.g. methylsulphonylamino or ethylsulphonylamino, or $C_{1-6}$dialkylsulphonylamino, e.g. dimethylsulphonylamino or diethylsulphonyl-amino groups. It will be appreciated that where two or more $R^{16}$ substituents are present, these need not necessarily be the same atoms and/or groups. The $R^{16}$ substituents may be present at any ring carbon atom away from that attached to the rest of the molecule of formula (1). Thus, for example, in phenyl groups any substituents may be present at the 2-, 3-, 4-, 5- or 6-positions relative to the ring carbon atom attached to the remainder of the molecule.

When the group $-(CH_2)_m-$ in compounds of formula (1) is a group $-(CH_2)_{2-6}$ it will be appreciated that such groups may be either straight or branched.

Heteroatoms represented by $Z^1$ and/or $Z^2$ in compounds of formula (1) include —O— or —S— atoms.

When the groups $R^3$ and $R^4$ in compounds of formula (1) are alkyl groups, they may be for example straight or branched $C_{1-6}$alkyl groups such as methyl or ethyl groups.

When the group $R^9$ or $R^{10}$ in compounds of formula (1) is an optionally substituted alkyl or alkenyl group it may be a straight or branched $C_{1-6}$ alkyl, e.g. methyl, ethyl, n-propyl i-propyl, n-butyl, i-butyl, n-pentyl or n-hexyl or $C_{2-6}$alkenyl e.g. ethenyl or 1-propenyl group optionally interrupted by one or more —O— or —S— atoms or —N($R^{12}$)— groups where $R^{12}$ is a hydrogen atom or an optionally substituted $C_{1-6}$alkyl group such as a methyl, ethyl or propyl group.

Optional substituents which may be present on such groups include one or more $C_{1-6}$alkoxy, $C_{1-6}$alkylthio, $C_{6-12}$aryl$C_{1-6}$alkoxy, aralkylthio, amino, substituted amino, carboxyl or $-CO_2R^{13}$ groups as defined above in connection with the group $R^1$, or an optionally substituted cycloalkyl, cycloalkenyl, aryl or heteroaryl group as defined below in connection with the groups $R^9$ and $R^{10}$.

When the group $R^9$, $R^{10}$ or $R^9$ and $R^{10}$ together with the carbon atom to which they are attached, is an optionally substituted cycloalkyl or cycloalkenyl group, it may be for example a $C_{3-8}$cycloalkyl, e.g. cyclopropyl, cyclopentyl or cyclohexyl, or $C_{3-8}$cycloalkenyl e.g. cyclopropenyl, cyclopentenyl or cyclohexenyl, group optionally substituted by one, two or more $C_{1-6}$alkyl, e.g. methyl or ethyl, $C_{1-6}$alkoxy, e.g. methyl or ethoxy, $C_{1-6}$alkylthio, e.g. methylthio, or hydroxyl groups. Alternatively, the group $R^9$ or $R^{10}$ may be an aryl or heteroaryl group as defined above for the group Ar.

The term Het in compounds of formula (1) may represent —O—, —S—, —S(O)—, —S(O)$_2$— or —N($R^{12}$)— where $R^{12}$ is a hydrogen atom or a $C_{1-6}$alkyl group as defined above.

When $R^{11}$ in compounds of formula (1) is an aliphatic group it may be for example an optionally substituted saturated or unsaturated straight or branched $C_{1-6}$alkyl chain optionally interrupted by one or more —O— or —S— atoms or groups selected from —N($R^{12}$)—, —CO—, —CON($R^{12}$)—, or —N($R^{12}$)CO—. Particular groups include optionally substituted methyl, ethyl, n-propyl, i-propyl, n-butyl, i-butyl, s-butyl, t-butyl, ethenyl, 1-propenyl, 1-butenyl or 2-butenyl groups. Optional substituents which may be present on groups of these types include one or more amino (—NH$_2$), substituted amino [for example a group —NR$^{17}$R$^{18}$ as described below in relation to the group X], $C_{6-12}$aryl, e.g. optionally substituted phenyl, $C_{6-12}$aryloxy e.g. optionally substituted phenoxy, [the optional substituents in each case being $R^{16}$ groups as defined above], $C_{3-8}$-cycloalkyl, e.g. cyclopentyl or cyclohexyl, $C_{3-8}$cycloalkoxy, e.g. cyclopentyloxy or cyclohexyloxy, carboxyl (—CO$_2$H) or —CO$_2$R$^{13}$ groups.

Cycloaliphatic groups represented by $R^{11}$ in compounds of formula (1) include optionally substituted $C_{3-8}$cycloalkyl and $C_{3-8}$cycloalkenyl groups, for example optionally substituted cyclopropyl, cyclobutyl, cyclopentyl, cyclohexyl, cyclopentenyl and cyclohexenyl groups. Optional substituents include those groups $R^{16}$ described above.

Heterocycloaliphatic groups represented by $R^{11}$ in the compounds of formula (1) include optionally substituted $C_{5-7}$heterocycloalkyl groups containing one or two heteroatoms selected from —O— or —S—, or a group —N($R^{12}$)—, for example optionally substituted piperazinyl, morpholinyl, pyrrolidinyl, tetrahydrofuranyl, tetrahydropyranyl, piperidinyl, or N-methylpiperidinyl groups. Optional substituents include those groups $R^{16}$ described above. The heterocycloalkyl groups represented by $R^{11}$ may be attached to the remainder of the molecule through any ring carbon atom.

When the group $R^{11}$ in compounds of formula (1) is an aromatic group it may be for example an optionally substituted mono- or bicyclic $C_{6-12}$aryl group, for example an optionally substituted phenyl or 1- or 2-naphthyl group. Optional substituents which may be present on groups of this type include those $R^{16}$ substituents described above.

Heteroaromatic groups represented by the group $R^{11}$ include mono- or bicyclic $C_{5-9}$heteroaromatic groups containing one, two or three heteroatoms selected from —O— or —S—, or —N($R^{12}$) groups. Particular examples include pyrrolyl, furanyl, thienyl, imidazolyl, oxazolyl, thiazolyl, 1-indolyl, 2-indolyl, 1-quinolinyl or 2-quinolinyl, pyrazolyl, 1-indolyl, 2-indolyl, 1-quinolinyl or 2-quinolinyl groups. Such groups may be optionally substituted, for example by one or more $R^{16}$ substituents. The heteroaromatic group may be connected to the remainder of the compound of formula (1) through any ring carbon atom, or where appropriate through a heteroatom or group —N($R^{12}$)—.

When X in the compounds of formula (1) represents a substituted amino group it may be for example a group of formula —NR$^{17}$R$^{18}$, where $R^{17}$ and $R^{18}$, which may be the same or different, is each a hydrogen atom (with the proviso that when one of $R^{17}$ or $R^{18}$ is a hydrogen atom, the other is not) or an optionally substituted straight or branched alkyl group, optionally interrupted by one or more —O— or —S— atoms or —N($R^{12}$)— or aminocarbonyloxy [—NHC(O)O—] groups or $R^{17}$ and $R^{18}$, together with the nitrogen atom to which they are attached, may form an optionally substituted $C_{3-6}$cyclic amino group optionally possessing one or more other heteroatoms selected from —O— or —S—, or —N($R^{12}$)— groups.

When $R^{17}$ and/or $R^8$ is an alkyl group it may be for example a $C_{1-6}$alkyl group such as a methyl, ethyl, n-propyl, i-propyl, n-butyl, i-butyl, s-butyl, or t-butyl group, optionally interrupted by one or more —O— or —S— atoms, or —N($R^{13}$)— or aminocarbonyloxy groups and may be for example a methoxymethyl, ethoxymethyl, ethoxymethyl, ethoxyethyl or ethylaminocarbonyloxymethyl group. The optional substituents which may be present on such groups include hydroxyl (—OH), carboxyl (—CO$_2$H), esterified carboxyl (—CO$_2$R$^{13}$), carboxamido (—CONH$_2$), substituted carboxamido, e.g. a group —CONR$^7$R$^{18}$ where NR$^{17}$R$^8$ is as defined herein, amino (—NH$_2$), substituted amino, for example a group of formula —NR$^{17}$R$^{18}$, aminosulphonylamino, for example —N($R^{12}$)SO$_2$NH$_2$ or —N($R^{12}$)SO$_2$NR$^{17}$R$^{18}$ or aryl, e.g. $C_{6-12}$ aryl such as phenyl, optionally substituted by one, two or more $R^{16}$ substituents selected from those listed above.

Particular examples of cyclic amino groups represented by —NR$^{17}$R$^{18}$ include morpholinyl, imidazolyl, piperazinyl, pyrrolyl, oxazolyl, thiazolyl, pyrazolyl, pyrrolidinyl, pyridinyl and pyrimidinyl groups.

When the group X is a substituted hydroxyl group it may be for example a group —OR$^{11}$ where $R^{11}$ is as defined above, other than a hydrogen atom.

When X is linked to the atom or group Het in $R^5$ to form a chain —X-Alk-R$^5$—, the optionally substituted alkylene chain represented by Alk may be an optionally substituted straight or branched $C_{2-9}$ alkylene chain, for example an ethylene, propylene or butylene chain. Optional substituents present on the alkylene chain include those described above in relation to the alkyl group represented by $R^2$. In compounds of this type, the group X is —$N(R^{12})$—, where $R^{12}$ is as defined above. The group $R^5$ is —Het—$C(R^9)(R^{10})$— where Het, $R^9$ and $R^{10}$ are as defined above.

Salts of compounds of formula (1) include pharmaceutically acceptable salts, for example acid addition salts derived from inorganic or organic acids, such as hydrochlorides, hydrobromides, hydroiodides, p-toluene sulphonates, phosphates, sulphates, perchlorates, acetates, trifluoroacetates, propionates, citrates, malonates, succinates, lactates, oxalates, tartarates and benzoates.

Salts may also be formed with bases. Such salts include salts derived from inorganic or organic bases, for example alkali metal salts such as sodium or potassium salts, alkaline earth metal salts such as magnesium or calcium salts, and organic amine salts such as morpholine, piperidine, dimethylamine or diethylamine salts.

Prodrugs of compounds of formula (1) include those compounds, for example esters, alcohols or amines, which are convertible, in vivo, by metabolic means, e.g. by hydrolysis, reduction, oxidation or transesterification.

When the group R in compounds of the invention is an esterified carboxyl group, it may be a metabolically labile ester of formula —$CO_2R^{13}$ where $R^{13}$ may be an ethyl, benzyl, phenylethyl, phenylpropyl, 1- or 2-naphthyl, 2,4-dimethylphenyl, 4-t-butylphenyl, 2,2,2-trifluoroethyl, 1-(benzyloxy)-benzyl, 1-(benzyloxy)ethyl, 2-methyl-1-propionyloxypropyl, 2,4,6-trimethylbenzoyloxymethyl or pivaloyloxymethyl group.

When the group R in compounds of formula (1) is a —$P(O)(X^1R^7)X^2R^8$ group it may in particular be a $P(O)(OR^7)OR^8$, e.g. a —$P(O)(OH)OR^8$ group, or a —$P(O)(SH)OR^8$ or —$P(O)(OH)SR^8$ group. Examples of such groups include —$P(O)(OCH_3)OCH_3$, —$P(O)(OCH_2CH_3)OCH_2CH_3$, —$P(O)(OH)OH$, —$P(O)(OH)SH$, —$P(O)(SH)OH$, —$P(O)(OH)OCH_3$, —$P(O)(OH)SCH_3$, —$P(O)(OH)OCH_2CH_3$, —$P(O)(OH)OPh$, —$P(O)(OH)SPh$, —$P(O)(OH)OCH_2Ph$ or —$P(O)(OH)SCH_2Ph$, where Ph is a phenyl group optionally substituted by one or more substituents $R^{16}$.

In the compounds of formula (1) the group $R^1$ may in particular be a $C_{1-6}$alkyl group such as a methyl group, an aralkyl group such as benzyl group, an arylthioalkyl group such as a phenylthiomethyl group or a heteroarylthioalkyl group such as thienylthiomethyl, pyridinylthiomethyl or pyrimidinylthiomethyl group or is especially a hydrogen atom.

The group $R^2$ in compounds of formula (1) may in particular be an ArO—, ArS—, $ArCH_2$—, $Ar(CH_2)_2$—, $Ar(CH_2)_3$—, $Ar(CH_2)_4$—, $ArOCH_2$—, $ArO(CH_2)_2$—, $ArO(CH_2)_3$—, $ArO(CH_2)_4$—, $ArSCH_2$—, $ArS(CH_2)_2$—, $ArS(CH_2)_3$—, or $ArS(CH_2)_4$— group, where Ar is as defined for formula (1). Particular groups of these types are those wherein Ar is an optionally substituted phenyl, pyrrolyl, furanyl, thienyl, imidazolyl, oxazolyl, thiazolyl, pyrazolyl, pyridinyl or pyrimidinyl group. Optional substituents present on Ar groups of these types include one, two or more $R^{16}$ substituents as defined above.

The groups $R^3$ and $R^4$ in compounds of formula (1) may each in particular be a methyl group, or, especially, a hydrogen atom.

The group $R^5$ in compounds of formula (1) may in particular be a group —$C(R^9)(R_{10})Het$-$R^{11}$ where $R^9$ and $R^{10}$ are the same. Particular compounds of this type are those wherein $R^9$ and $R^{10}$ is each the same and is each an optionally substituted alkyl, alkenyl, cycloalkyl, cycloalkenyl, aryl or heteroaryl group.

In another group of compounds of formula (1) the group $R^5$ may be a group —$C(R^9)(R^{10})Het$-$R^{11}$ where $R^9$ is an aliphatic, cycloaliphatic, heterocycloaliphatic, aromatic or heteroaromatic group as described above for compounds of formula (1).

The group X in compounds of formula (1) may be in particular an amino (—$NH_2$) or —$NR^{17}R^{18}$ group. Particular —$NR^{17}R^{18}$ groups are —$NHR^{18}$ groups. Groups of this type include those where $R^{18}$ is a $C_{1-6}$alkyl group, for example a methyl, ethyl, or n-propyl group, optionally interrupted by one or more —O— or —S— atoms or —$N(R^{12})$ [e.g. —NH— or —$N(CH_3)$—] or aminocarbonyloxy groups and optionally substituted by a hydroxyl, carboxyl, carboxyalkyl, e.g. carboxymethyl, carboxamido, amino, —$NR^{17}R^{18}$, [for example di-$C_{1-6}$alkyl amino such as dimethylamino, $C_{1-6}$alkylamino such as methylamino, or $C_{3-6}$ cyclic amino such as morpholinyl, pyrrolidinyl or pyridinyl] or phenyl optionally substituted by one, two or more $R^{16}$ substituents.

A particularly useful group of compounds according to the invention is that of formula (1) wherein $R^5$ is a group —$C(R^9)(R^{10})$ Het-$R^{111}$ where Het is —$S(O)p$ and $R^9$, $R^{10}$ and $R^{11}$ are as defined for formula (1). Compounds of this type wherein Het is —S— are particularly useful.

A further particularly useful group of compounds of formula (1) are those wherein X is an amino or substituted amino group. Particularly useful compounds of this type are those wherein X is —$NHCH_3$ or, especially, —$NH_2$.

In general, in compounds of formula (1) the groups $R^1$, $R^3$ and $R^4$ is each preferably a hydrogen atom.

In a further preference, the group R in compounds according to the invention is a —CONHOH or a —$CO_2H$ group or a metabolically labile ester thereof, or a group $P(O)(OH)OR^8$. In a particular preference, however, R is a —$CO_2H$, —$P(O)(OH)_2$ or, especially, a —CONHOH group.

An especially useful group of compounds according to the invention has the formula (1a)

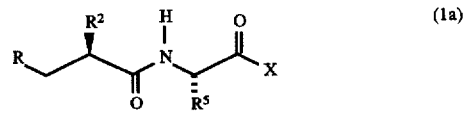

wherein R, $R^2$, $R^5$ and X are as defined for formula (1); and the salts, solvates, hydrates and prodrugs thereof.

A particularly useful group of compounds of formula (1a) are those wherein R represents a —CONHOH, —$CO_2H$ or —$P(O)(OH)_2$ group; $R^2$ and $R^5$ are as defined for formula (1); X is an amino (—$NH_2$) or substituted amino group; and the salts, solvates, hydrates and prodrugs thereof.

Particularly useful compounds of formula (1a) are those wherein $R^5$ is a group —$C(R^9)(R^{10})S(O)pR^{11}$. Compounds of this type in which $R^5$ is a —$C(R^9)(R^{10})SR^{11}$ group are especially useful.

Other useful compounds of formula (1a) include those wherein $R^2$ represents an ArO—, ArS—, $ArCH_2$—, $Ar(CH_2)_2$—, $Ar(CH_2)_3$—, $Ar(CH_2)_4$—, $ArOCH_2$—, $ArO(CH_2)_2$—, $ArO(CH_2)_3$—, $ArO(CH_2)_4$—, $ArSCH_2$, $ArS(CH_2)_2$, $ArS(CH_2)_3$—, or $ArS(CH_2)_4$— group, where Ar is as defined for formula (1), and especially is an optionally substituted phenyl group. Particularly useful groups of this type are optionally substituted phenylethyl, phenylpropyl, or phenylbutyl groups. Optionally substituted phenylpropyl groups are especially useful. Optional substituents on the phenyl group may be one, two or more R groups as defined for compounds of formula (1). Particularly useful substituted phenyl groups are 4-substituted phenyl groups.

In the compounds of formula (1a) X may be a —$NH_2$ group or a group —$NR^{17}R^{18}$ as defined for compounds of formula (1), particularly a —$NHR^{18}$ group.

An especially useful group of compounds according to the invention has the formula (1a) wherein $R^2$ is an optionally substituted phenyl$C_{3-6}$alkyl group, especially an optionally substituted phenylpropyl or phenylbutyl group, $R^5$ is a group —$C(R^9)(R^{10})SR^{11}$ where $R^9$ and $R^{10}$ is each the same and is each an optionally substituted $C_{1-6}$ alkyl group, and $R^{11}$ is as defined for formula (1); and X is an amino (—$NH_2$) or —$NHR^{18}$ group, particularly where $R^{18}$ is an optionally substituted $C_{1-6}$alkyl group. Compounds of this type wherein $R^5$ is a group —$C(CH_3)_2SR^{11}$ are particularly useful, especially where the group $R^{11}$ is a hydrogen atom or an optionally substituted saturated $C_{1-6}$ alkyl chain. In compounds of this last type X is preferably an amino (—$NH_2$) group or a —$NHCH_3$ group.

In a still further useful group of compounds of formula (1a), R is a —CONHOH, —$CO_2H$ or —$P(O)(OH)_2$ group, $R^2$ is an optionally substituted phenylpropyl group, $R^5$ is a group —$C(CH_3)_2SR^{11}$ where $R^{11}$ is a hydrogen atom or an optionally substituted $C_{1-6}$alkyl group, and X is an amino (—$NH_2$) or —$NHR^{18}$ group where $R^{18}$ is an optionally substituted $C_{1-6}$ alkyl group. Compounds of this type wherein R is a —CONHOH group are particularly useful; as are those compounds wherein $R^{11}$ is a hydrogen atom or a methyl group; and those compounds wherein $R^{18}$ is a hydrogen atom or a methyl group.

One further group of compounds according to the invention has the formula (1a) wherein R and $R^2$ are as defined for formula (1), $R^5$ is a group —$C(CH_3)_2SH$ or —$C(CH_3)_2SCH_3$ and X is —$NH_2$ or —$NHCH_3$. Particularly useful compounds of this type are those wherein R is a group —CONHOH, —$CO_2H$ or —$P(O)(OH)_2$ and $R^2$ is a group ArO—, ArS—, $ARCH_2$—, $Ar(CH_2)_2$—, $Ar(CH_2)_3$—, $Ar(CH_2)_4$, $ArOCH_2$, $ArO(CH_2)_3$—, $ArO(CH_2)_4$—, $ArSCH_2$—, $ArS(CH_2)_2$—, $ArS(CH_2)_3$— or $ArS(CH_2)_4$— group, where Ar is as defined for formula (1). Especially useful compounds of this type are those wherein Ar is an optionally substituted phenyl group. Particularly useful compounds are those where $R^2$ is an optionally substituted phenylethyl, phenylbutyl or, especially, phenylpropyl group.

In compounds of the above described types, $R^2$ is preferably an optionally substituted phenylpropyl group and $R^5$ is preferably a group —$C(CH_3)_2SCH_3$. In these compounds, R is preferably —$CO_2H$ or —$P(O)(OH)_2$ or is especially —CONHOH. X is preferably —$NH_2$ or —$NHCH_3$.

Important compounds according to the invention include:

[4-(N-Hydroxyamino)-2(R)-[3-(4-chlorophenyl)propyl] succinyl]-L-[S-(methyl)penicillamine] N-methylamide;

[4-(N-Hydroxyamino)-2(R)-[3-(4-chlorophenyl)propyl] succinyl]-L-[S-(methyl)penicillamine] amide;

[4-(N-Hydroxyamino)-2(R)-[3-(4-chlorophenyl)propyl] succinyl]-L-penicillamine amide;

{4-(N-Hydroxyamino)-2(R)-[3-(4-chlorophenyl)propyl] succinyl}-L-[S-(methyl)penicillaminesulphone]-N-methylamide;

{4-(N-Hydroxyamino)-2(R)-[3-(4-chlorophenyl)propyl] succinyl}-L-[S-(methyl)penicillaminesulphoxide]-N-methylamide;

{4-(N-Hydroxyamino)-2(R)-[3-(4-chlorophenyl)propyl] succinyl}-L-penicillamine-N-methylamide;

and the salts, solvates, hydrates and prodrugs thereof.

The compounds according to the invention may be prepared by the following general processes, more specifically described in the Examples hereinafter. In the description and formulae below the groups R, $R^1$, $R^2$, $R^3$, $R^4$, $R^5$ and X are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable amino or hydroxyl protecting groups include benzyl, benzyloxycarbonyl or t-butyloxycarbonyl groups. These may be removed from a protected derivative by catalytic hydrogenation using for example hydrogen in the presence of a metal catalyst, for example palladium on a support such as carbon in a solvent such as an alcohol e.g. methanol, or by treatment with trimethylsilyl iodide or trifluoroacetic acid in an aqueous solvent. Suitable carboxyl protecting groups include benzyl groups, which may be removed from a protected derivative by the methods just discussed, or alkyl groups, such as a t-butyl group which may be removed from a protected derivative by treatment with trifluoroacetic acid in an aqueous solvent. Other suitable protecting groups and methods for their use will be readily apparent. The formation of the protected amino, hydroxyl or carboxyl group may be achieved using standard alkylation or esterification procedures, for example as described below.

Thus according to a further aspect of the invention a compound of formula (1) may be prepared by coupling an acid of formula (2)

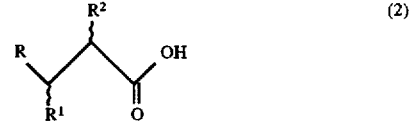

or an active derivative thereof, with an amine of formula (3)

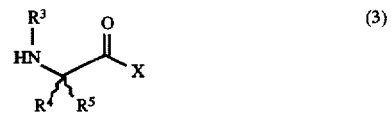

followed by removal of any protecting groups.

Active derivatives of acids of formula (2) include for example acid anhydrides, or acid halides, such as acid chlorides.

The coupling reaction may be performed using standard conditions for amination reactions of this type. Thus, for example the reaction may be achieved in a solvent, for example an inert organic solvent such as an ether, e.g. a cyclic ether such as tetrahydrofuran, an amide e.g. a substituted amide such as dimethylformamide, or a halogenated hydrocarbon such as dichloromethane at a low temperature, e.g. −30° C. to ambient temperature, such as −20° C. to 0° C., optionally in the presence of a base, e.g. an organic base such as an amine, e.g. triethylamine or a cyclic amine such as N-methylmorpholine. Where an acid of formula (2) is used, the reaction may additionally be performed in the presence of a condensing agent, for example a diimide such as N,N'-dicyclohexylcarbodiimide, or 1-(3-dimethylaminopropyl)-3-ethylcarbodi-imide, advantageously in the presence of a triazole such as 2-hydroxybenzotriazole. Alternatively, the acid may be reacted with a chloroformate for example ethylchloroformate, prior to reaction with the amine of formula (3).

Free hydroxyl or carboxyl groups in the starting materials of formulae (2) [where R is —CONHOH or CO$_2$H] and (3) may need to be protected during the coupling reaction. Suitable protecting groups and methods for their removal may be those mentioned above. Where R in the intermediates of formula (2) is a —P(O)(X$^1$R$^7$)X$^2$R$^8$ group, at least one of R$^7$ or R$^8$ is other than a hydrogen atom. Conveniently, each of R$^7$ and R$^8$ is an optionally substituted alkyl, aryl or aralkyl group. Such groups, when present in compounds of the invention may be cleaved as described below to yield other compounds of the invention wherein R$^7$ and/or R$^8$ is each a hydrogen atom.

It will be appreciated that where a particular stereoisomer of formula (1) is required, this may be obtained by resolution of a mixture of isomers following the coupling reaction of an acid of formula (2) and an amine of formula (3). Conventional resolution techniques may be used, for example separation of isomers by chromatography e.g. by use of high performance liquid chromatography. Where desired, however, appropriate homochiral starting materials may be used in the coupling reaction to yield a particular stereoisomer of formula (1). Thus, in particular process a compound of formula (1a) may be prepared by reaction of a compound of formula (2a)

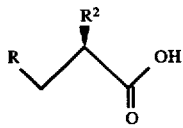
(2a)

with an amine of formula (3a)

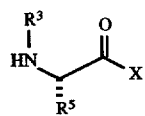
(3a)

as described above

Intermediate acids of formula (2) wherein R is a carboxyl or esterified carboxyl group or a group —P(O)(X$^1$R$^7$)X$^2$R$^8$ or —SR$^6$ may be prepared from a corresponding ester of formula (4)

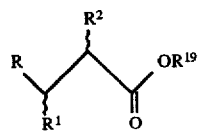
(4)

where R$^{19}$ is an alkyl group, for example a methyl or t-butyl group, using for example trifluoroacetic acid, or, when R$^{19}$ is an aralkyl group, such as a benzyl group, by hydrogenolysis, for example by reaction with hydrogen in the presence of a metal catalyst, e.g. palladium, on a support such as carbon in a solvent such as an alcohol, e.g. methanol optionally at an elevated pressure and temperature.

An ester of formula (4) where R is a carboxyl or esterified carboxyl group may be prepared by esterification of the corresponding acid of formula (5)

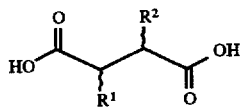
(5)

using an appropriate acyl halide, for example an acyl chloride in a solvent such as an alcohol, e.g. methanol at a low temperature, e.g. around 0° C.

Acids of formula (5) may be prepared by alkylation of a compound of formula (6)

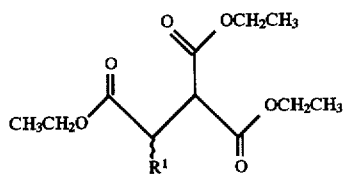
(6)

with an appropriate halide, e.g. a compound R$^2$Hal, where Hal is a halogen atom such as a chlorine or bromine atom in the presence of a base, for example an alkoxide such as sodium ethoxide in a solvent such as an alcohol, e.g. ethanol at ambient temperature, followed by decarboxylation using for example concentrated hydrochloric acid at an elevated temperature, e.g. the reflux temperature.

Intermediates of formula (6) are either known compounds or may be prepared by methods analogous to those used for the preparation of the known compounds.

Intermediate esters of formula (4) where R is a —P(O)(X$^1$R$^7$)X$^2$R$^8$ group may be prepared by reaction of an acrylate R$^1$CHC(R$^2$) COR$^{19}$ with a phosphite:P(OR$^{20}$)(X$_1$R$^7$)X$^2$R$^8$ [where R$^{20}$ is a leaving group, for example a silyl group such as a trialkylsilyl group e.g. a trimethylsilyl group] at an elevated temperature.

Acrylates of formula R$^1$CHC(R$^2$)COR$^{19}$ may be prepared by reaction of a mono-ester HOOCCH(R$^2$)COOR$^{19}$ with an aldehyde R$^1$CHO or a polymer thereof e.g. paraformaldehyde or paraldehyde in the presence of a base, for example an organic base such as piperidine. The reaction may be performed in a solvent, such as pyridine, optionally at an elevated temperature.

Mono-esters of formula HOOCCH(R$^2$)COOR$^{19}$ may be prepared by hydrolysis of the corresponding di-ester R$_{19}$OOCCH(R$^2$)COOR$^{19}$ using a base, for example an alkali hydroxide, in an inert solvent such as dioxane at a low temperature e.g. around 0° C. The di-esters for use in this reaction may be prepared by alkylation of the corresponding malonates of formula R$_{19}$OOCCH$_2$COOR$^{19}$ with a halide R$^2$Hal [where Hal is a halogen atom such as a chlorine or bromine atom] in the presence of a base, e.g. a hydride such as sodium hydride in a solvent such as tetrahydrofuran at ambient temperature. Malonates of formula R$^{19}$OOCCH$_2$COOR$^{19}$ are either known compounds or may be prepared by methods analogous to those used for the preparation of the known compounds.

Intermediate phosphites of formula P(OR$^{20}$)(X$^1$R$^7$)X$^2$R$^8$ may be prepared by reaction of a phosphite HP(O)(X$^1$R$^7$)X$^2$R$^8$ with an appropriate amine (R$^{20}$)$_2$NH e.g. a silazane, at an elevated temperature, e.g. the reflux temperature. Phosphites of formula HP(O)(X$^1$R$^7$)X$^2$R$^8$ are either known compounds or may be prepared by methods analogous to those used for the preparation of the known compounds.

Intermediates of formula (4) where R is a —SR$^6$ group am either known compounds or may be prepared from known starting materials of formula R$^6$SCH(R$^1$)CH(CO$_2$CH$_2$CH$_3$)$_2$ by using a similar series of reactions to those just described for the preparation of compounds of formula (4) where R is a carboxyl group.

In another process, intermediate acids of formula (2) wherein R is a —P(O)(X$^1$R$^7$)X$^2$R$^8$ group may be prepared by reaction of an acid R$^2$CH$_2$CO$_2$H with a phosphonate P(O)(X$^1$R$^7$)(X$^2$R$^8$)CH$_2$OR$^{21}$ where R$^{21}$ is a leaving group, for example a trifluoromethylsulphonyloxy group in the presence of a base such as n-butyllithium in a solvent such as tetrahydrofuran. Phosphonates for use in this reaction may be prepared from the corresponding compound P(O)(X$^1$ R$^7$)(X$^2$R$^8$)CH$_2$OH by reaction with paraformaldehyde in the presence of a base such as triethylamine at an elevated temperature followed by reaction with a halide $R^{21}$Hal in the presence of a base such as sodium hydride in a solvent such as an ether. Phosphonates $P(O)(X^1R^7)(X^2R^8)CH_2OH$ and acids $R^2CH_2CO_2H$ for use in the above reactions are either known compounds or may be prepared by methods analogous to those used for the preparation of the known compounds.

Intermediate acids of formula (2) wherein R is a —$CONHOR^6$ group or a protected derivative thereof may be prepared by reaction of an anhydride of formula (7)

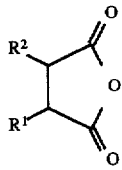
(7)

with a hydroxylamine such as O-benzylhydroxylamine or $NH_2OR^6$ where $R^6$ is an acyl group in a solvent such as tetrahydrofuran at a low temperature, e.g. around $-20°$ C., followed where desired by removal of the protecting group as described above.

The intermediate anhydrides of formula (7) may be prepared for example by heating for example at the reflux temperature, a diacid of formula (5) where R is —$CO_2H$ with an acyl chloride such as acetyl chloride.

The homochiral acids of formula (2a) may be prepared according to another feature of the invention by oxidation of an oxazolidinone of formula (8)

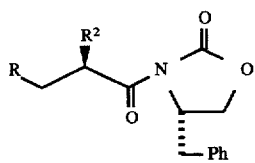
(8)

(where Ph is a phenyl group) using an oxidising agent such as peroxide, e.g. hydrogen peroxide in a solvent such as an ether e.g. a cyclic ether such as tetrahydrofuran, at a low temperature, e.g. around $0°$ C. followed by treatment with a base, such as lithium hydroxide, at an elevated temperature.

The compounds of formula (8) may be prepared by reaction of an acyl halide $RCH_2CH(R^2)COHal$ (where Hal is a halogen atom such as a chlorine, bromine or iodine atom) with a solution of (S)-4-(phenylmethyl)-2-oxazolidinone in the presence of a base such as n-butyl lithium in a solvent such as tetrahydrofuran at a low temperature, e.g. around $-78°$ C.

Acyl halides $RCH_2CH(R^2)COHal$ may be prepared by treatment of the corresponding known acids $RCH_2CH(R^2)CO_2H$ with conventional halogenating agents for example thionyl halides under standard reaction conditions.

Intermediates of formula (3) are either known compounds or may be prepared from known amino acid starting materials using standard methods, for example by employing a series of substitution reactions to manipulate the groups $R^5$ and X as described in the Examples hereinafter or for example as described by L. Wessjohann et al, Chem. Ber. 1992, 125, 867–882.

Compounds of formula (1) may also be prepared by interconversion of other compounds of formula (1). Thus, for example, a compound of formula (1) wherein R is a —$CONHOR^6$ group may be prepared by reaction of a corresponding acid of formula (1) wherein R is a —$CO_2H$ group or an active derivate thereof (for example an acid chloride or an acid anhydride) with hydroxylamine or an O-protected derivative or a salt thereof or a reagent $R^6ONH_2$ where $R^6$ is an acyl group. The reaction may be performed using the reagents and conditions described above in the preparation of compounds of formula (1) from the starting materials of formulae (2) and (3).

In another interconversion process, compounds of formula (1) wherein R is —$CO_2H$ and/or X contains a —$CO_2H$ group may be prepared by hydrolysis of the corresponding esterified compounds (for example where R is a —$CO_2R^{13}$ group and/or X contains a similar group) using conventional procedures, for example by treatment with a base, e.g. an alkali metal hydroxide such as lithium hydroxide in a solvent such as an aqueous alcohol, e.g. aqueous methanol, or by treatment with an acid such as a mineral acid, e.g. hydrochloric acid in the presence of a solvent, e.g. dioxane.

Similarly esters of formula (1), for example where R is a $CO_2R^{13}$ group and/or X contains a —$CO_2R^{13}$ group may be prepared by reaction of the corresponding acids, where R is a —$CO_2H$ group and/or X contains a —$CO_2H$ group or an active derivative thereof, with an alcohol $R^{13}OH$ using standard conditions.

In another interconversion process, a compound of formula (1) wherein $R^5$ is a group —$C(R^9)(R^{10})SR^{11}$ may be oxidised to a corresponding compound where $R^5$ is a group —$C(R^9)(R^{10})SOR^{11}$ or —$C(R^9)(R^{10})SO_2R^{11}$ using an oxidising agent, for example a peroxy-monosulphate such as potassium peroxymonosulphate, in a solvent such as an aqueous alcohol at ambient temperature or a peroxy-acid in a halogenated hydrocarbon solvent such as dichloromethane at a low temperature, e.g. around $-78°$ C.

The compounds according to the invention are potent and selective inhibitors of gelatinase and advantageously have a long duration of action when administered orally. The activity and selectivity of the compounds may be determined by the use of appropriate enzyme inhibition tests for example as described in Example A hereinafter or by administration to mice as described hereinafter in Example B. In our tests using this approach, compounds according to the invention have been shown to inhibit gelatinase with Ki values in the picomolar-nanomolar range and to have around a 100 fold or greater selectivity for gelatinase over stromelysin, and around a 1000-fold or greater selectivity for gelatinase over collagenase.

The compounds according to the invention can be expected to be of use in the prophylaxis or treatment of diseases or disorders in which stromelysin, collagenase and, in particular, gelatinase have a role. Thus for example the compounds of formula (1) may be of use in the prophylaxis or treatment of musculo-skeletal disorders, for example arthritic diseases such as rheumatoid arthritis, osteoarthritis and septic arthritis, and to be of use to prevent tumour cell metastasis and invasion. The compounds may therefore be of use in the treatment of cancer, particularly in conjunction with radiotherapy, chemotherapy or surgery, or in patients presenting with primary tumours, to control the development of tumour metastasis. Particular cancers may include breast, melanoma, lung, head, neck or bladder cancers. Other uses to which the compounds of the invention may be put, include use for prevention of myelin degradation in the central and peripheral nervous system, for example in the treatment of multiple sclerosis, use for controlling peridontal diseases such as gingivitis, and use in tissue remodelling.

The compounds according to the invention can also be expected to be of use in the prophylaxis or treatment of angiogenic diseases. Such diseases may be characterised by the pathological growth of new capillaries [see, for example Folkman, J. and Klagsbrun, M. Science 235, 442–447

(1987) and Moses, M. A. and Langer, R. Bio/Technology 9, 630–634 (1991)]. Particular angiogenesis dependent diseases include solid tumours and arthritic diseases as described above, and, additionally, psoriasis, eye diseases such as the proliferative retinopathies, neovascular glaucoma and ocular tumours, angiofibromas, and hemangiomas.

For use according to this aspect of the invention, the compounds of formula (1) may be formulated in a conventional manner, optionally with one or more physiologically acceptable carriers, diluents or excipients.

Thus according to a further aspect of the invention we provide a pharmaceutical composition comprising a compound of formula (1) and a pharmaceutically acceptable diluent, carrier or excipient.

In a still further aspect the invention provides a process for the production of a pharmaceutical composition comprising bringing a compound of formula (1) into association with a pharmaceutically acceptable diluent, carrier or excipient.

Compounds for use according to the present invention may be formulated for oral, buccal, parental or rectal administration or in a form suitable for nasal administration or administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles; and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formula (1) may be formulated for parental administration by injection e.g. by bolus injection or continuous infusion. Formulations for injection may be presented in unit dosage form. The compositions for injection may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of formula (1) may also be formulated in rectal compositions such as suppositories or retention enemas, e.g. containing conventional suppository bases such as cocoa butter or other glycerides.

In addition to the formulations described above the compounds of formula (1) may also be formulated as a depot preparation. Such long acting formulations may be administered by implantation or by intramuscular injection.

For nasal administration or administration by inhalation the compounds for use according to the present invention are conveniently delivered in the form of an aerosol spray presentation for pressurised packs or a nebuliser, with the use of suitable propellant, e.g. dichlorodifluoro methane, trichlorofluoromethane, dichlorotetrafluoromethane, carbon dioxide or other suitable gas, or mixture of gases.

The compositions may, if desired, be presented in a pack or dispenser device which may contain one or more unit dosage forms containing the active ingredient. The pack or dispenser device may be accompanied by instructions for administration.

The doses of compounds of formula (1) used in the above applications will vary depending on the disease or disorder and condition of the patient to be treated but in general may be in the range around 0.05 mg to 100 mg/kg body weight, particularly from about 0.5 mg to 50 mg/kg body weight. Dosage units may be varied according to the route of administration of the compound in accordance with conventional practice.

DESCRIPTION OF SPECIFIC EMBODIMENTS

The invention is further illustrated in the following non-limiting Examples.

In the Examples, the following abbreviations are used:
RT—room temperature
DMF—dimethylformamide
THF—tetrahydrofuran
TFA—trifluoroacetic acid
$CH_2Cl_2$—dichloromethane
$Et_2O$—diethylether

EXAMPLE A

The activity and selectivity of the compounds of the invention may be determined as described below.

All enzyme assays to determine Ki values were performed using the peptide substrate Dnp-Pro-Leu-Gly-Leu-Trp-Ala-D-Arg-$NH_2$. [M. Sharon Stock and Robert D. Gray, JBC 264, 4277–81, 1989]. The enzymes cleave at the Gly-Leu bond which can be followed fluorimetrically by measuring the increase in Trp fluorescence emission associated with the removal of the quenching dinitrophenol (Dnp) group.

Essentially, enzyme (e.g. gelatinase, stromelysin, collagenase) at 0.08–2 nM; a range of inhibitor concentrations (0.1–50×Ki) and substrate (approx. 20 μm) are incubated overnight in 0.1M Tris/HCl buffer, pH 7.5, containing 0.1M NaCl, 10 mM $CaCl_2$ and 0.05%. Brij 35 at either room temperature or 37° C. depending on the enzyme. The reaction is stopped by adjusting the pH to 4 using 0.1M sodium acetate buffer and the fluorescence read at an excitation wavelength of 280 nm and emission wavelength of 346 nm.

$K_i$ values can be established using the equation for tight-binding inhibition:

$$V_i = \frac{V_o}{2[E]} \left( \sqrt{(K_{i(app)} + [I])^2 + 2(K_{i(app)} - [I])[E] + [E]^2} - (K_{i(app)} + [I] - [E]) \right)$$

where $V_O$ is the initial rate of reaction in the absence of inhibitor, $V_i$ is the initial rate in the presence of inhibitor, [E] is the total enzyme concentration and [I] the total inhibitor concentration in the reaction mixture.

For stromelysin and collagenase, $K_i$ (app) was assumed to approximate to the true $K_i$ as $[S]<<K_m$ for the substrate hydrolysis. For gelatinase the $K_i$ was determined by performing the analyses at several substrate concentrations. A plot of $K_i$(app) vs. [S] then gave the true $K_i$ as the value of the y-axis intercept.

The following results were obtained with compounds according to the invention:

| | Ki (nM) | | |
|---|---|---|---|
| | Collagenase | Stromelysin-1 | Gelatinase-72KD |
| Compound of Example No. | | | |
| 3a) | 26.3 | 5.3 | 0.005 |
| 3b) | 122 | 3.6 | 0.027 |
| 4 | 20.7 | 5.92 | 0.005 |

EXAMPLE B

The oral activity of the compounds according to the invention may be determined using the mouse pleural cavity assay described below. This assay measures the ability of compounds of the invention when adminstered orally to inhibit a subsequent inoculation of gelatinase into the mouse pleural cavity.

A 2 ml solution of the test compound (for example around 25 µm/Kg) in an appropriate solvent (e.g. 50% polyethylene glycol (PG)) plus a variable proportion of dimethyl sulphoxide (DMSO) (if required) is administered orally. After an interval of up to 24 hrs. 0.4 ml of a mixture of an equal volume (2.2 ml) of the enzyme gelatinase A (72K form at a concentration of 20 nM) and radiolabelled [$^{14}$C]-gelatin (at an approximate concentration of 10 µM i.e. 500 times molar excess) is injected into the pleural cavity and maintained at 4° C. After 35 min mice are overdosed with anaesthetic, the contents of the pleural cavity aspirated and the aspirates cleared by centrifugation at 4° C. then diluted to 15% in trichloroacetic acid (TCA) and left overnight at 4° C. The resulting TCA precipitate is then separated by centrifugation and radioactivity in each supernatant measured by scintillation counting. Results are expressed as a % inhibition of enzyme activity calculated by comparing the radioactivity measured for each test compound with a control value obtained by performing the same assay in the absence of a gelatinase inhibitor. Thus, for example, the compound of Example 3b) gave 100% inhibition when adminstered orally at the above dose.

The ability of compounds of the invention to prevent tumour cell invasion may be demonstrated in a standard mouse model. Thus, briefly, nude mice may be inoculated with a tumour cell line showing gelatinase-dependent invasion and the ability of compounds according to the invention to reduce subsequent lung tumour colonisation may be evaluated in accordance with standard procedures. In out tests, compounds according to the invention, when administered orally in a single dose at 100 mg/kg to mice in the above model have reduced lung tumour colonisation to negligible levels for periods of twelve hours duration or longer.

In general, compounds according to the invention are non-toxic at pharmaceutically useful doses. Thus, for example, when the compounds were administered to mice at the doses described above no adverse effects were observed.

INTERMEDIATE 1

N-tert-butoxycarbonyl-L-penicillamine

To a solution of L(+)-penicillamine (24 g; 161 mmol) in 10% w/v aqueous sodium carbonate solution (300 ml)was added di-tert-butyl dicarbonate (35.1 g; 161 mmol) in tert-butanol (300 ml). After stirring the reaction mixture for 18 hr at RT, the volume was reduced by approximately one half under reduced pressure and the pH was adjusted to 2 using 1N hydrochloric acid. The resulting slurry was extracted several times with Et$_2$O, the ethereal layers being combined, dried (MgSO$_4$) and evaporated to give the title compound (36.7 g) as a clear gum. $\delta_H$ (CDCl$_3$) 8.65 (1H, br s), 5.50 (1H, d), 4.35 (1H, d), 2.00 (1H, br s), 160 (3H, s), 1.50 (9H, s), and 1.45 (3H, s).

INTERMEDIATE 2

N-tert-butoxycarbonyl-L-penicillamine-N-methylamide

A solution in anhydrous dimethylformamide (250 ml) of Intermediate 1 (11.69 g; 33.5 mmol), N-hydroxybenzotriazole (4.53 g; 33.5 mmol), methylamine hydrochloride (11.3 g; 167.5 mmol), N-methylmorpholine (20.6 ml; 184 mmol), 1-(3-dimethylaminopropyl)-3-ethyl carbodiimide hydrochloride (7.1 g; 36.9 mmol) and a trace of 4-dimethylaminopyridine was stirred at RT under an atmosphere of nitrogen for 18 hr. The reaction mixture was poured into 10% w/v aq.citric acid (600 ml) and extracted into Et$_2$O (600 ml). The organic layer was separated, washed with 10% w/v aq. NaHCO$_3$ solution (500 ml), dried (MgSO$_4$) and evaporated. Following chromatography (SiO$_2$; EtOAc 20–50% in hexane), the title compound (6.36 g) was obtained as a clear glass. $\delta_H$ (CDCl$_3$) 6.85 (1H, m), 5.75 (1H, d), 4.15 (1H, d), 2.75 (3H, d), 2.50 (1H, br s), 1.50 (3H, s), 1.45 (9H, s), and 1.35 (3H, s).

INTERMEDIATE 3

N-tert-butoxycarbonyl-L-[S-(methyl)penicillamine]-N-methyl-amide

To a solution of Intermediate 2 (1g; 3.82 mmol) in 2N aq. NaOH/CH$_3$OH (10 ml/30 ml) was added iodomethane (1.18 ml; 19 mmol) in CH$_3$OH (4 ml). After stirring at RT for 2 hr, the reaction mixture was concentrated to one quarter volume, then partitioned between Et$_2$O and brine. The organic layer was washed with 10% w/v aq. citric acid, dried (MgSO$_4$) and evaporated to give the title compound (810mg ) as a colourless glass. δH (CDCl$_3$) 6.80 (1H, m), 5.65 (1H, d), 4.20 (1H, d), 2.80 (3H, s), 2.10 (3H, s), 1.45 (9H, s), 1.40 (3H, s), and 1.30 (3H, s).

INTERMEDIATE 4 a) L-[S-(Methyl)penicillamine]-N-methylamide trifluoroacetate

A solution of Intermediate 3 (810mg; 2.93 mmol) in TFA/CH$_2$Cl$_2$ (10 ml/10 ml) was stirred at RT for 2 hr. The solvent was then removed under reduced pressure with the aid of a toluene/THF azeotrope. The title compound (855 mg) was obtained as a yellow tinged glass in quantitative yield. $\delta_H$ (CDCl$_3$) 8.4 (3H, br s), 7.9 (1H, q), 4.20 (1H, s), 2.80 (3H, d), 2.0 (3H, s), 1.45 (3H, s), and 1.35 (3H, s).

b) 3-(3-Aminopropylthio)-2(S)-benzyloxycarbonylamino-3-methylbutanoic acid trifluoracetate From Intermediate 14 (6.4 g; 14.5 mmol) in TFA/CH$_2$CL$_2$ (6 ml/6 ml), using the method described to obtain Intermediate 4a), to give the title compound (6.04 g).

INTERMEDIATE 5

3-[4-Phenoxybutanoyl]-4(S)-benzyl-2-oxazolidinone

4-Phenoxybutyric acid (1.22 g, 6.8 mmol, 1.2 equiv) was heated to reflux with thionyl chloride (0.66 ml, 1.07 g, 9.0 mmol, 1.6 equiv) for 30 min. The excess thionyl chloride was then removed under vacuum, the residue dissolved in THF (10 ml), and added to a cold (−78° C.) solution of lithiated (S)-4-benzyl-2-oxazolidinone [prepared from the oxazolodinone (1 g, 5.6 mmol) and n-butyllithium (1.6M solution, 4.23 ml, 6.8 mmol, 1.2 equiv) in THF (25 ml)]. The reaction mixture was stored for 2 hr at −78° C., then quenched with a 1:1 mixture of saturated brine and 10% HCl acid (20 ml). The mixture was allowed to warm to RT and partitioned between ethyl acetate and water. The layers were separated and the aqueous layer washed twice with ethyl acetate. The combined organic layers were washed once with brine, once with sodium bicarbonate solution, dried (MgSO$_4$) and the solvent removed under vacuum to give a brown oil which was recrystallised (ethyl acetate) to give the title compound (0.897 g) as a white solid. δ$_H$ (CDCl$_3$) 7.35–7.17 (m, 7H), 6.94–6.86 (m, 3H), 4.66 (m, 1H), 4.18 (m, 2H), 4.06 (t, 2H), 3.30 (dd, 1H), 3.16 (t, 2H 2.25 (dd, 1H), and 2.18 (m, 2H).

INTERMEDIATE 6

3-(1-Oxo-2(R)-t-butyl-acetyl-2-phenoxyethyl)-4(S)-benzyl-2-oxazolidinone

Sodium hexamethyldisilazide (1.0M solution in THF, 4.2 ml, 4.2 mmol, 1.4 equiv) was added dropwise to a solution of Intermediate 5 (1.01 g, 3 mmol) in THF (25 ml) at −78° C. Stirring was continued at this temperature for 1 hr, then (t)-butyl bromoacetate (1.74 g, 1.44 ml, 9 mmol, 3 equiv) was added. The temperature was allowed to rise to −20° C. over a period of 4 hr. The reaction was then cooled to −78° C. and quenched with a mixture of brine and 10% HCl acid (1:1, 20 ml). The reaction was warmed to RT and partitioned between water and ethyl acetate. The aqueous layer was washed twice with ethyl acetate and the combined organic layers washed once with sodium bicarbonate solution, once with brine, dried (MgSO$_4$) and the solvent removed in vacuo to give a yellow oil. Chromatography (SiO$_2$ Merck 9385; ethyl acetate-hexane, 1:4) afforded the title compound (0.90 g) as a white solid. δ$_H$ (CDCl$_3$) 7.40–7.18 (m, 7H), 6.95–6.80 (m, 3H), 4.62 (m, 1H), 4.42 (m, 1H), 4.28–3.96 (m 3H), 3.87 (t, 1H), 3.33 (dd, 1H), 2.91 (dd, 1H), 2.72 (dd, 1H), 2.56 (dd, 1H), 2.26–1.94 (m, 2H), and 1.42 (s, 9H).

INTERMEDIATE 7 a) 2-(R)-(2-Phenoxyethyl)succinic acid-4-(t)-butyl monoester

Hydrogen peroxide (0.91 ml, 8 mmol, 4 equiv 27.5 wt%) was added to a cold (0° C.) solution of Intermediate 6 (0.90 g, 2 mmol) in THF/water (4:1, 50 ml). The solution was stirred for 5 min then a solution of lithium hydroxide (80 mg, 2 mmol) in water (10 ml) was added dropwise. The reaction was stirred for 2 hr at 0° C. then most of the THF was removed in vacuo. The mixture was partitioned between water and CH$_2$Cl$_2$, and the aqueous layer was extracted with ethyl acetate (x3). The combined organic layers were dried (MgSO$_4$) and the solvent removed to give the title compound (0.60 g) as a colourless oil which was used without further purification.

b) 2-(R)-[3-(4-methoxyphenyl)propyl]succinic acid-4-(t)-butyl monoester

The above intermediate was prepared in a similar manner to Intermediate 7a) starting from 4-(4-methoxyphenyl) butyric acid.

c) 2-(R)-[3-(4-methylphenyl)propyl]succinic acid-4-(t)-butyl monoester

The above intermediate was prepared in a similar manner to Intermediate 7a) starting from 4-(4-methylphenyl)butyric acid.

INTERMEDIATE 8

2-(R)-[3-(4-Chlorophenyl)propyl]succinic acid-4-(t)-butyl monoester

The title compound was prepared in a similar manner to Intermediate 7a) starting from 4-(4-chlorophenyl)butyric acid (see also J R Porter et al, "Organometallic Reagents in Organic Synthesis", SmithKline Beecham Research Symposium, 25th–26th Mar., 1993, Robinson College, Cambridge, UK).

INTERMEDIATE 9

Methyl 2-chloro-2-cyclopropylidino acetate

To a solution of sodium methoxide in methanol [prepared from sodium (8.22 g) in methanol (250 ml)] was added 1-chloro-1-(trichloroethenyl)-cyclopropane (15 ml) and the mixture heated under reflux for 87 hr. The reaction mixture was cooled, treated with ice-water (100 ml), brine (100 ml), extracted with Et$_2$O (4×250 ml), the combined organic layers dried (MgSO$_4$) and concentratd in vacuo. The residue was dissolved in CH$_2$Cl$_2$ (250 ml) before adding the ion exchange resin (Dowex 50W-X8) (10.0 g) and some 3 Å molecular sieves. The mixture was stirred at RT for 48 h, filtered through celite and concentrated in vacuo. The residue was chromatographed (SiO$_2$; EtOAc-Pentane, 1:8), to give the title compound (5.64 g) as a white solid.

INTERMEDIATE 10

Methyl 2-azido-2-(1-methylthiocyclopropyl)acetate

To a suspension of sodium thiomethoxide (1.43 g) in THF (35 ml) at −78° C. was added Intermediate 9 (2.58 g) in THF (25 ml), the mixture stirred at −78° C. for 4 hr, then warmed up to −20° C. and stored at −18° C. The mixture was treated with 2.0M hydrochloric acid in Et$_2$O (1eq), stirred at −20° C. for 5 hr, treated with saturated ammonium chloride and extracted with Et$_2$O. The combined organic layer was dried (MgSO$_4$) and concetnrated/n vacuo to give methyl 2-chloro-2-(1-methylthiocyclopropyl) acetate (2.23 g) as a colourless oil.

A mixture of this compound (2.23 g) aliquat® 336 (5.23 ml), and sodium azide (2.22 g) in water (15 ml) was stirred vigorously at 55° C. for 48 hr. The reaction mixture was extracted with Et$_2$O, the combined organic layer washed with brine, dried (MgSO$_4$) and concentrated in vacuo. Chromatography (SiO$_2$; Et$_2$O-pentane, 1:6) gave the title compound (0.7492 g) as a colourless oil.

INTERMEDIATE 11

2-Azido-2-(1-methylthiocyploroyl)ethanamide

A solution of Intermediate 10 (0.72 g) in methanol (20 ml) was heated with aqueous sodium hydroxide (2.0M; 2.7 ml) and water (2.7 ml) and the mixture stirred at RT overnight. The solvent was removed in vacuo, the residue dissolved in water, extracted with Et$_2$O then acidified to pH3 with aqueous hydrochloric acid (2.0M). The solution was extracted with chloroform, the combined organic layer dried ($MgSO_4$) and concentrated in vacuo to give 2-azido-2-(1-thiomethyl)cyclopropylidino acetic acid (0.56 g) as a thick pale lemon oil.

A solution of the acid (0.56 g) in THF (25 ml) was treated with N-methymorpholine (413 μl) and isobutylchloroformate (430 μl) at −30° C. and the mixture stirred at −30° to −25° C. for 1 hr. Concentrated aqueous ammonia (≈35%; 1.6 ml) was added and the stirred reaction mixture allowed to warm up to RT overnight. The solvent was removed/n vacuo and the residue partitioned between saturated aqueous sodium bicarbonate and ethyl acetate. The aqueous layer was extracted with ethyl acetate and $CH_2Cl_2$, then acidified to pH3 with aqueous HCl (2.0M), extracted with $CH_2Cl_2$ and the organic layer dried ($MgSO_4$). Chromatography ($SiO_2$; 5% methanol in $CH_2Cl_2$) afforded the title compound (0.50 g) as a pale brown oil.

INTERMEDIATE 12

2-Amino-2-(1-methylthiocyclopropyl)ethanamide trifluoroacetate

A solution of Intermediate 11 (0.48 g) and trifluoroacetic acid (25 ml) in degassed methanol (47.5 ml) was treated with 10% palladium on carbon (90.0 mg) and the mixture stirred at RT under an atmosphere of hydrogen for 18 hr. The solvent was removed in vacuo to give the compound (528 mg) as a very pale buff solid.

INTERMEDIATE 13

N-tert-Butoxycarbonyl-L-(S-methyl)penicillamide

A mixture of Intermediate 1 (14.7 g; 59 mmol), ethyl chloroformate (8.2 ml; 67.7 mmol), and N-methylmorpholine (10.8 ml; 96.8 mmol) in dry THF (250 ml) was activated for 1 hr at −20° C. The reaction mxiture was cooled to −30° C., a solution of 2N ammonia in methanol (100 ml; 200 mmol) was added slowly by syringe and the mixture allowed to warm to RT overnight. The volatiles were removed, the residue was partitioned between ethyl acetate and aqueous citric acid, the organic layer washed with aqueous $NaHCO_3$, separated, dried ($MgSO_4$) then evaporated to yield N-tert-butoxycarbonyl-L-penicillamide (11.04 g).

To a portion of this thiol (5.02 g; 22.25 mmol) in 2N NaOH (60 ml) and ethanol (180 ml) was added methyliodide (6.91 ml; 111 mmol) and the mixture stirred at RT for 18 hr. The solution was concentrated in vacuo, partitioned between $Et_2O$ and brine, dried ($MgSO_4$) and concentrated in vacuo. Column chromatography ($SiO_2$; 4% $CH_3OH$ in $CH_2Cl_2$) yielded the title compound (3.03 g) as an off-white solid.

INTERMEDIATE 14

2-(S)-Benzyloxycarbonylamine-3-[3-butyloxycarbonyl-amino)propylthio]-3-methylbutanoic acid To L-penicillamine (15.75 g; 105.8 mmol) was added a solution of KOH (12.4 g; 222.2 mmol) in water (250 ml). When the solution was complete, $Et_2O$ (100 ml) was added and the solution cooled to 0° C. Benzyl chloroformate (14.9 ml; 105.8 mmol) was added dropwise and the stirred reaction mixture allowed to warm to RT. The layers were separated, the aqueous layer acidified to pH 1–1.5 with 1N hydrochloric acid, extracted with $CH_2Cl_2$ (×3) and dried ($MgSO_4$). The solvent was removed in vacuo to yield N-benzyloxycarbonyl-L-penicillamine (21.27 g).

To a portion of this compound (7.8 g; 27.6 mmol) in 2N NaOH/ethanol (1:1) was added a solution of N-benzyloxycarbonyl-3-chloro-1-propylamine (6.4 g; 33.1 mmol) [prepared from 3-chloropropylamine hydrochloride (5 g; 38 mmol) in 10% NaOH/t-butanol (2/3; 100 ml) and di-t-butyldicarbonate (9.2 g; 42.3 mmol) in t-butanol (50 ml)] in ethanol and the mixture was stirred overnight at 40° C. The solvent was evaporated in vacuo, the residue partitioned between $Et_2O$ and 10% aqueous citric acid, the organic layer washed with brine, dried ($MgSO_4$) and the solvent removed in vacuo to yield the title compound (6.4 g).

INTERMEDIATE 15

3-(S)-Benzyloxycarbonylamino-2,2-dimethylperhydro-5-thiazoline-4-one

To a cold (0° C.) solution of Intermediate 4b) (1.04 g; 2.23 mmol) in dry DMF (400 ml) were added N-methylmorpholine (735 μl; 669 mmol), 1-(3-dimethylaminopropyl)-3-ethylcarbodiimide (642 mg; 3.34 mmol), 1-hydroxybenzotriazole hydrate (452 mg; 3.34 mmol) and a catalytic amount of 4-dimethylaminopyridine, the stirred reaction mixture allowed to warm to RT overnight then dried ($MgSO_4$). The solvent was removed in vacuo and the residue purified by column chromatography ($SiO_2$; 10–20% ethyl 35 acetate/hexane) to yield the title compound (3.17 g).

INTERMEDIATE 16

3-Amino-2,2-dimethylperhydro-5-thiazocine-4-one hydrobromide

A portion of Intermediate 15 (350 mg) was treated with a solution of 30% HBr in acetic acid (10 ml). The solvent was evaporated to dryness and the residue partitioned between water and $Et_2O$. The aqueous layer was separated then freeze-dried to yield the title compound (308 mg) as a pale yellow solid.

EXAMPLE 1 a) [4-t-Butoxy-2(R)-[3-(4-chlorophenyl)propyl] succinyl]-L-[S-(methyl)penicillamine]-N-methylamide A solution in anhydrous DMF (3 ml) of Intermediate 8 (948 mg; 2.9 mmol), Intermediate 4a) (852 mg; 2.93 mmol) N-hydroxy-benzotriazole (397 mg; 2.93 mmol), N-methylmorpholine (983 μl; 8.79 mmol), 1-(3-dimethylaminopropyl)-3-ethyl carbodiimide hydrochloride (614 mg; 3.19 mmol) and a trace amount of 4-dimethylaminopyridine was stirred at RT under an atmosphere of nitrogen for 18 hr. The reaction mixture was poured into 10% w/v aq.citric acid (100 ml) and extracted into diethyl ether (1 00 ml). The organic layer was washed with 10% w/v aq. $NaHCO_3$, separated, dried ($MgSO_4$) and evaporated. The residue was chromatographed ($SiO_2$; 2–4% $CH_3OH$ in $CH_2Cl_2$) to give the title compound (904 mg) as a white solid. $\delta_H$ ($CDCl_3$) 7.25 (2H, d), 7.10 (2H, d), 4.50 (1H, d), 2.80 (3H, d), 2.30–2.7 (5H, m), 2.10 (3H, s), 1.75–1.30 (4H, m), 1.45 (9H, s), 1.40 (3H, s), and 1.30 (3H, s).

The following compounds were prepared in a similar manner to the compounds of Example 1a).

b) [4-t-Butoxy-2(R)-(2-phenoxyethyl)succinyl]-L-[S-(methyl) penicillamine]-N-methylamide From Intermediate 7a and Intermediate 4.

c) 4-t-Butoxy-2(R)-[3-4(4-chlorolphenyl)propyl [succinyl-2-(S)-amino-3-hydroxy-3-methyl butanamide From Intermediate 8 and 2-(S)-amino-3-hydroxy-3-methyl butanamide.

d) {4-t-Butoxy-2(R)-[3-(4-chlorophenyl)propyl] succinyl}-L-(1-methylthiocyclopropyl)glycinamide From Intermediate 8 and Intermediate 12.

e) {4-t-Butoxy-2(R)-[3-4-methoxyphenyl)propyl] succinyl}-L-(1-methylthiocyclopropyl)glycinamide From Intermediate 7b and Intermediate 12.

f) t-Butoxy-N4-[3-(S)-(2,2-dimethyl-4-oxoperhydro-5-thiazocinyl)]-3-(R)-[3-(4-chlorophenyl)propyl] succinamoate From Intermediate 8 and Intermediate 16. The title compound was obtained as a colourless glass.

EXAMPLE 2 a) [4-Hydroxy-2(R)-[3-(-4-chlorophenyl]succinyl]-L-[S-(methyl)penicillamine]-N-methylamide A solution of the compound of Example 1a) (452 mg; 0.933 mmol) in a mixture of TFA (10 ml) and water (0.5 ml) was left to stand at 4° C. for 18 hr. The solvent was evaporated with the aid of a toluene/THF azeotrope. The title compound (400 mg) was obtained as a colourless foam in quantitative yield. $\delta_H$ (CDCl$_3$) 10.20 (1H, br s), 7.65 (1H, d), 7.25 (2H, d), 7.05 (2H, d), 6.95 (1H, q), 4.65 (1H, d), 2.80 (3H, d), 2.80–2.40 (5H, m), 2.05 (3H, s), 1.40–1.70 (4H, m), 1.30 (3H, s), and 1.25 (3H, s).

The following compounds were prepared in a similar manner to the compound of Example 2a).

b) {4-Hydroxy-2(R)-[3-(4-chlorophenyl)propyl] succinyl}-2(S)-2-amino-3-hydroxy-3-methylbutamamide From the compound of Example 1c).

c) {4-Hydroxy-2(R)-[3-(4-chlorophenyl)propyl] succinyl}-L-(1-methylthiocyclopropyl)glycinamide From the compound of Example 1d).

d) {4-Hydroxy-2(R)-[3-(4-methoxyphenyl)propyl] succinyl}-L-(1-methylthiocyclopropyl)glycinamide From the compound of Example 1e).

e) Hydrogen-N4-[3-(S)-(2,2-dimethyl-4-oxoperhydro-5-thiazocinyl)]-3-(R) -[3-(4-chlorophenyl)propyl]succinamoate From the compound of Example 1f.

EXAMPLE 3 a) [4-(N-Hydroxyamino)-2(R)-[3-(4-chlorophenyl) propyl]succinyl]-L-[S-(methyl)penicillamine]-N-methylamide To a solution in anhydrous THF of the compound of Example 2a) (400 mg; 0.933 mmol) at −20° C. was added N-methylmorpholine (209 μl; 1.87 mmol), and ethyl chloroformate (133 μl; 1.12 mmol). After 1 hr, O-trimethylsilylhydroxylamine (3.75 mmol) was added and the reaction mixture was allowed to warm to RT overnight. The solvent was evaporated under reduced pressure and the residue was partitioned between ethyl acetate and 10% w/v aq. citric acid. The organic layer was separated, dried (MgSO$_4$) and evaporated. The residue was purified (SiO$_2$; 5–10% CH$_3$OH in CH$_2$Cl$_2$) to give the title compound (165 mg) as a white solid. $\delta_H$ (CD$_3$OD) 7.25 (2H, d), 7.15 (2H, d), 4.50 (1H, s), 2.90 (1H, m), 2.70 (3H, s), 2.50–2.70 (2H, m), 2.40 (1H, dd), 2.20 (1H, dd), 2.05 (3H, s), 1.40–1.70 (4H, m), 1.40 (3H, s), and 1.35 (3H, s).

The following compounds were prepared by coupling (as described in Example 1) Intermediate 8, 7b) or 7c) and the appropriate amide to yield the corresponding t-butoxy derivatives which were hydrolysed (as described in Example 2) to give the corresponding carboxylic acid derivatives. The acid derivatives were then treated as described in Example 3a) to yield the following N-hydroxyamino derivatives:

b) [4-(N-Hydroxyamino)-2(R)-[3-(4-chlorophenyl) propyl]-1-succinyl]-L-penicillamine amide $\delta_H$ (CD$_3$OD) 7.25 (2H, d), 71.5 (2H, d), 4.50 (1H, s), 2.90 (1H, m), 2.60 (2H, m), 2.40 (1H, dd), 2.20 (1H, dd), 1.40 (4H, m), 1.45 (3H, s), and 1.40 (3H, s).

c) [4-(N-Hydroxyamino )-2(R)-[3(4-chlorophenyl) propyl]-succinyl]-L-[S-(4-morpholinoethyl) penicillamine]-N-methylamide $\delta_H$ (CD$_3$OD) 7.25 (2H, d), 7.15 (2H, d), 4.50 (1H, s), 3.70 (4H, t), 2.90 (1H, m), 2.15–2.80 (13H, m), 1.40–1.70 (4H, m), 1.40 (3H, s), and 1.40 (3H, s).

d) [4-(N-Hydroxyamino)-2(R)-[3-(4-chlorophenyl) propyl]-succinyl]-L-penicillamine-N-methylamide.

δH (CD$_3$OD) 7.25 (2H, d), 7.15 (2H, d), 4.50 (1H, s), 2.90 (1H, m), 2.70 (3H, s), 2.60 (2H,m), 2.40 (1H, dd), 2.20 (1H, dd), 1.45–1–65 (4H, m), 1.40 (3H, s), and 1.35 (3H, s).

e) N-[4-(N-hydroxyamino)2(R)-[3-(4-chlorophenyl) propyl]succinyl]-2(S)-2-amino-3-hydroxy-3-methylbutanamide $\delta_H$ (CD$_3$OD) 1.23 (s, 3H, CH$_3$), 1.28 (s, 3H, CH$_3$), 1.40–1–64 (m, 4H, CH$_2$CH$_2$), 2.20 (dd, 1H, J6.24, 14.6 Hz, CH), 2.39 (dd, 1H, J8.28, 14.6Hz, CH), 2.56–2.62 (m, 2H, CH$_2$), 2.82–2.98 (m, 1H, CH), 4.39 (s, 1H, CH), and 7.14–7.22 (AB, d, 4H, J18.80 Hz, Ar).

f) {4-(N-Hydroxyamino-2-(R)-[3-(4-chlorophenyl) propyl]succinyl}-L-(1-methylthiocyclopropyl) glycinamide $\delta_H$ (CD$_3$OD) 0.897 (m, 2H), 1.08 (m, 1H), 1.25 (m, 1H), 1.4–1.7 (m, 3H), 2.152 (s, 3H), 2.184 (dd, OH, 1H, J7.7, 14.0 Hz), 2.368 (dd, 1H, J=7.7 Hz, 14.0 Hz), 2.578 (m, 2H), 2.85 (m, 1H), 4.29 (s, 1H), 7.15 (d, 2H, J8.5 Hz), and 7.227 (d, 2H, J8.5 Hz).

g) N-{4-(N-Hydroxyamino)-2(R)-[3-(4-methoxyphenyl propyl]succinyl}-L-(1-methylthiocyclopropyl)glycinamide $\delta_H$ (CD$_3$OD) 0.89 (m, 2H, cyclopropyl CH), 1.03 (m, 1H, cyclopropyl CH), 1.22 (m, 1H), 1.4–1.7 (m, 4H), 2.184 (dd, O1H, J 7.8, 14.5 Hz), 2.367 (dd, 1H, J7.8, 14.5 Hz), 2.528 (m, 2H), 2.846 (m, 1H), 3.743 (s, 3H), 4.324 (s, 1H), 6.789

(d, 2H, J6.0 Hz), and 7.067 ppm (d, 2H, J6.0 Hz). Ω overlapped with another signal.

h) {4-(N-Hydroxyamino)-2(R)-[3-(4-methoxyphenyl)propyl]succinyl}-L-[S-(methyl)penicillamine]amide $\delta_H$ (CD$_3$OD) 6.90 (2H, d), 6.80 (2H, d), 4.55 (1H, m), 3.75 (3H, s), 2.85 (1H, m), 2.50 (2H, m), 2.40 (1H, dd), 2.20 (1H, dd), 2.10 (3H, s), 1.60 (4H, m), 1.40 (3H, s), and 1.35 (3H, s).

i) {4-(N-Hydroxyamino)-2(R)-[3-(4-methylphenyl)propyl]succinyl}-L-[S-(methyl)penicillamine]amide $\delta_H$ (CD$_3$OD) 7.0 (4H, s), 4.50 (1H, d), 2.90 (1H, m), 2.55 (2H, m), 2.40 (1H, dd), 2.30 (3H, s), 2.20 (1H, dd), 2.05 (3H, s), 1.65 (4H, m), 1.40 (3H, s), and 1.35 (3H, s).

j) N4-Hydroxy-N1-[3-(S)—(2,2-dimethyl-4-oxoperhydro-5-thiazocinyl)]-2-(R)-[3-(4-chlorophenyl)propyl]succinimide From the compound of Example 2e). $\delta_H$ (CD$_3$OD) 7.25 (2H, d), 7.15 (2H, d), 5.15 (1H, s), 3.85 (1H, m), 3.15 (1H, m), 2.95 (1H, m), 2.75 (2H, m), 2.60 (2H, m), 2.40 (1H, dd), 2.20 (1H, dd), 1.85 (2H, br m), 1.40–1.70 (4H, m) and 1.35 (6H, s).

EXAMPLE 4

{4-(N-Hydroxyamino)-2(R)-[3-(4-chlorophenyl)propyl]succinyl}-L-[S-(methyl)penicillaminesulphone]-N-methylamide To a solution of the compound of Example 3a) (452 mg; 0.933 mmol) in methanol (10 ml) at 0° C. was added a solution of Oxone® (1.844 g; 3 mmol) in water (5 ml). The reaction mixture was allowed to warm to RT over 3 days, then diluted with water and extracted into chloroform. The organic layer was washed with brine, dried (MgSO$_4$) and evaporated to give a quantitative recovery of the title compound (482 mg) as a white solid. $\delta_H$ (CD$_3$OD) 7.25 (2H, d), 7.10 (2H, d), 5.0 (1H, s), 2.95 (3H, s), 2.90 (1H, m), 2.65 (3H, s), 2.60 (2H, m), 2.45 (1H, dd), 2.15 (1H, dd), 1.40–1.70 (10H, m).

EXAMPLE 5

{4-N-Hydroxyamino)-2(R)-[3-(4chlorophenyl)propyl]succinyl}-L-[S-(methyl)pennicillaminesulphoxide]-N-methylamide To a solution of the compound of Example 3a (183.4 mg; 0.379 mmol) in CH$_2$Cl$_2$ (10 ml) at −78° C., was added dropwise a solution of metachloroperbenzoic acid (78.3 mg; 0.454 mmol) in CH$_2$Cl$_2$ (1ml). The reaction mixture was then allowed to warm to RT and stirred for 2 hours. The solvent was removed under reduced pressure and the residue was purified (SiO$_2$; 4–5% CH$_3$OH in CH$_2$Cl$_2$), to give the title compound (117.3 mg) as a 50:50 mixture of diastereoisomers. δ(CD$_3$OD) 7.25 (2H, m), 7.15 (2H, m), 4.70 (0.5H, s), 4.65 (0.5H, s), 2.90 (1H, m), 2.70 (3H, 2s), 2.10–2.65 (7H, m), 1.40–1.65 (4H, m), 1.40 (1.5H, s), 1.30 (2s) and 1.25 (1.5H, s).

EXAMPLE 6

{4-t-Butoxy-2-(R)-[3-(4-chlorophenyl)propyl]succinyl}-L-(S)-methyl)pennicillamide A solution of Intermediate 13 (2.174 g; 8.30 mmol) in TFA/CH$_2$Cl$_2$ (20 ml/20 ml) was stirred at RT for 1 hr. The solvent was then removed under reduced pressure with the aid of a toluene/THF/CH$_2$Cl$_2$ azeotrope to yield L-(S-methyl)penicillamide trifluoroacetate (quantitative) as a clear gum.

A solution in anhydrous DMF of the penicillamide (8.3 mmol), Intermediate 8 (7.9 mmol), N-hydroxybenzotriazole (1.083 g; 8 mmol), N-methylmorpholine (2.24 ml; 20 mmol), 1-(3-dimethylaminopropyl)-3-ethyl carbodiimide hydrochloride (1.67 g; 8.3 mmol) and a trace of amount of 4-dimethylaminopyridine was stirred at RT under an atmosphere of nitrogen for 18 hr. The reaction mixture was poured into 10% w/v aqusous citric acid and extracted into Et$_2$O. The organic layer was separated, washed with 10% w/v aqusous NaHCO$_3$ solution, dried (MgSO$_4$) and evaporated to yield the title compound (2.9 g) as a white foam.

EXAMPLE 7

[4-(N-Hydroxyamino)-2(R)-[3-(4-chlorophenyl)propyl]-succinyl]-L-[S-(methyl)penicillamine]amide A solution of the compound of Example 6 (6.16 mmol 2.9 g) in a mixture of TFA (40 ml) and water (2 ml) was left to stand at RT for 1 hr. The solvent was removed with the aid of a toluene/THF/CH$_2$Cl$_2$ azeotrope to yield {4-hydroxy-2-(R)-[3-(4-chloropohenyl)propyl]succinyl}-L-(S-methyl)penicillamide (quantitative) as a white solid.

To a solution in anhydrous THF of the acid (6.16 mmol) at −20° C. was added N-methylmorpholine (1.035 ml; 9.24 mmol), and ethyl chloroformate (8.22 µl; 6.78 mmol). After 40 min, O-trimethylsilylhydroxylamine (1.32 ml; 12.32 mmol) was added and the reaction mixture was allowed to warm to RT overnight. The solvent was evaporated under reduced pressure and the residue was partitioned between ethyl acetate and methanol and 10% w/v aqueous citric acid. The organic layer was separated, dried (MgSO$_4$) and concentrated. A white solid appeared which was diluted with Et$_2$O and allowed to stand in the refrigerator overnight to yield, after filtration, the title compound (1.92 g) as a white semi-crystalline material.

$\delta_H$ (CD$_3$OD) 7.25 (2H, d), 7.15 (2H, d), 4.50 (1H, s), 2.90 (1H, m), 2.60 (2H, m), 2.40 (1H, dd), 2.20 (1H, dd), 2.10 (3H, s), 1.60 (4H, m), 1.40 (3H, s), and 1.35 (3H, s).

I claim:

1. A compound of formula (1)

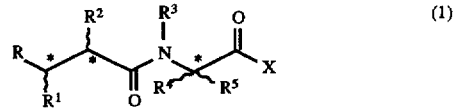

wherein wherein R represents —CONHOH;

R$^1$ is selected from the group consisting of a hydrogen atom and an optionally substituted C$_{1-6}$alkyl, C$_{2-6}$alkenyl, phenyl, 1-naphthyl, 2-naphthyl, phenylC$_{1-6}$alkyl, 1-naphthylC$_{1-6}$alkyl, 2-naphthylC$_{1-6}$alkyl, pyrrolylmethyl, furanylmethyl, thienylmethyl, imidazolylmethyl, oxazolylmethyl, thiazolylmethyl, pyrazolylmethyl, pyridinylmethyl, pyrimidinylmethyl, pyrrolylthiomethyl, furanylthiomethyl, oxazolylthiomethyl, thiazolylthiomethyl, pyrazolylthiomethyl, pyridinylthiomethyl, and pyrimidinylthiomethyl group;

R$^2$ is selected from the group consisting of ArO—, ArS—, —ArCH$_2$—, Ar(CH$_2$)$_2$—, Ar(CH$_2$)$_3$—, Ar(CH$_2$)$_4$—, ArOCH$_2$—, ArO(CH$_2$)$_2$—, ArO(CH$_2$)$_3$—,ArO(CH$_2$)

₄—, ArSCH₂, ArS(CH₂)₂—, ArS(CH₂)₃—, and ArS(CH₂)₄—, wherein Ar is an optionally substituted phenyl, pyrrolyl, furanyl, thienyl, imidazolyl, oxazolyl, thiazolyl, pyrazolyl, pyridinyl or pyrimidinyl group;

$R^3$ represents a hydrogen atom;

$R^4$ represents a hydrogen atom;

$R^5$ represents a group —C($R^9$)($R^{10}$)Het-$R^{11}$, wherein each $R^9$ and $R^{10}$, which may be the same or different, is an optionally substituted $C_{1-6}$alkyl or $C_{2-6}$alkenyl group optionally interrupted by one or more —O— or —S— atoms or —N($R^{12}$)— groups, wherein $R^{12}$ is a hydrogen atom or an optionally substituted $C_{1-6}$alkyl group, or an optionally substituted cyclopropyl, cyclopentyl, cyclohexyl, cyclopropenyl, cyclopentenyl, cyclohexenyl, phenyl, pyrrolyl, furanyl, thienyl, imidazolyl, oxazolyl, thiazolyl, pyrazolyl, pyridinyl or pyrimidinyl group, or $R^9$ and $R^{10}$ together with the carbon atom to which they are attached are linked together to form an optionally substituted cyclopropyl, cyclopentyl, cyclohexyl, cyclopropenyl, cyclopentenyl, or cyclohexenyl group; Het is —O—, —S(O)p— (wherein p is 0, 1 or 2) or —N($R^{12}$)—; and $R^{11}$ is a hydrogen atom or an optionally substituted $C_{1-6}$alkyl group, or a bond to the group Alk of X, as defined below; and X is an amino group, —NHR¹⁸ group where in $R^{18}$ is an optionally substituted $C_{1-6}$alkyl group optionally interrupted by one or more —O— or —S— atoms, an —N($R^{12}$)— or an aminocarbonyloxy group, or X is —N($R^{12}$)— which is linked through a group Alk to $R^5$ to form —N($R^{12}$)-Alk-Het—C($R^9$)($R^{10}$)— wherein Alk is an optionally substituted $C_{2-9}$alkylene chain and $R^{12}$, Het, $R^9$ and $R^{10}$ are as defined above for $R^5$;

or a pharmaceutically acceptable salt, solvate, or hydrate thereof.

2. A compound according to claim 1 wherein $R_1$ is a hydrogen atom.

3. A compound according to claim 1, wherein Ar is an optionally substituted phenyl group.

4. A compound according to claim 1, wherein $R^2$ is Ar(CH₂)₃—.

5. A compound according to claim 1, wherein each $R^9$ and R is a methyl group.

6. A compound according to claim 1, wherein Het is a —S— atom.

7. A compound according to claim 1, wherein X is an amino (—NH₂) or a N-methylamino group.

8. A compound according to claim 1, which is selected from the group consisting of {4-(N-hydroxyamino)-2(R)-[3-(4-chlorophenyl)propyl]succinyl}-L-[S-(methyl)penicillamine] N-methylamide;

{4-(N-hydroxyamino)-2(R)-[3-(4-chlorophenyl)propyl]succinyl}-L-[S-(methyl)penicillamine] amide;

{4-(N-hydroxyamino)-2(R)-[3-(4-chlorophenyl)propyl]succinyl}-L-penicillamine amide;

{4-(N-hydroxyamino)-2(R)-[3-(4-chlorophenyl)propyl]succinyl}-L-[S-(methyl)penicillaminesulphone]-N-methylamide;

{4-(N-hydroxyamino)-2(R)-[3-(4-chlorophenyl)propyl]succinyl}-L-[S-(methyl)penicillaminesulphoxide]-N-methylamide; and {4-(N-hydroxyamino)-2(R)-[3-(4-chlorophenyl)propyl]succinyl}-L-penicillamine-N-methylamide, or a pharmaceutically acceptable salt, solvate, hydrate or prodrug thereof.

9. A pharmaceutical composition comprising a compound according to claim 1 and a pharmaceutical diluent, carrier or excipient.

* * * * *